(12) United States Patent
Bennis et al.

(10) Patent No.: US 8,309,123 B2
(45) Date of Patent: Nov. 13, 2012

(54) PHARMACEUTICAL COMPOSITIONS AND METHODS FOR THE ORAL DELIVERY OF INSULIN

(75) Inventors: Farid Bennis, Casablanca (MA); Jean Jacques Serrano, Montpellier (FR)

(73) Assignee: Farid Bennis, Casablanca (MA)

(*) Notice: Subject to any disclaimer, the term of this patent is extended or adjusted under 35 U.S.C. 154(b) by 0 days.

(21) Appl. No.: 12/339,310

(22) Filed: Dec. 19, 2008

(65) Prior Publication Data

US 2009/0176691 A1 Jul. 9, 2009

(30) Foreign Application Priority Data

Dec. 19, 2007 (FR) ...................................... 07 59971

(51) Int. Cl.
*A61K 9/20* (2006.01)
*A61K 9/46* (2006.01)
*A61K 38/28* (2006.01)

(52) U.S. Cl. .......... 424/464; 424/465; 424/466; 514/5.9

(58) Field of Classification Search .................... None
See application file for complete search history.

(56) References Cited

U.S. PATENT DOCUMENTS

| | | | |
|---|---|---|---|
| 4,692,433 A | 9/1987 | Hostetler et al. | |
| 5,783,556 A * | 7/1998 | Clark et al. ........................ | 514/4 |
| 5,824,638 A | 10/1998 | Burnside et al. | |
| 5,843,887 A * | 12/1998 | Petit et al. ........................ | 514/6.5 |
| 6,071,539 A | 6/2000 | Robinson et al. .............. | 424/466 |
| 6,998,110 B2 * | 2/2006 | Dugger, III ..................... | 424/45 |
| 7,605,123 B2 * | 10/2009 | Radhakrishnan et al. ........ | 514/3 |
| 2002/0132757 A1 | 9/2002 | McCoy et al. | |
| 2003/0017203 A1 | 1/2003 | Crotts et al. | |
| 2003/0145347 A1 * | 7/2003 | Lanahan et al. .............. | 800/278 |
| 2003/0229010 A1 * | 12/2003 | Ekwuribe ........................ | 514/3 |
| 2004/0258623 A1 * | 12/2004 | Xu et al. ........................ | 424/46 |
| 2006/0258561 A1 * | 11/2006 | Balschmidt et al. ............. | 514/3 |
| 2006/0293219 A1 * | 12/2006 | Ekwuribe et al. ................. | 514/3 |
| 2007/0134332 A1 * | 6/2007 | Turnell et al. ................. | 424/486 |
| 2007/0154559 A1 | 7/2007 | Pai et al. | |
| 2010/0151009 A1 * | 6/2010 | Levchik ........................ | 424/451 |

FOREIGN PATENT DOCUMENTS

| | | |
|---|---|---|
| IE | 36225 | 9/1976 |
| WO | WO85/05029 | 11/1985 |
| WO | WO97/33531 | 9/1997 |
| WO | WO 0044350 A1 * | 8/2000 |
| WO | WO02/072075 | 9/2002 |
| WO | WO 2006017541 A2 * | 2/2006 |
| WO | WO2006127361 | 11/2006 |
| WO | WO2007/032018 | 3/2007 |

OTHER PUBLICATIONS

Brange et al. Acta. Pharm. Nord. 4(3): 149-158, 1992.*
Cernea et al.; "Noninjectable Methods of Insulin Administration"; Timely Top Med. Cardiovasc. Dis. 1-25, 2006.

* cited by examiner

*Primary Examiner* — Jeffrey E Russel
(74) *Attorney, Agent, or Firm* — Wood, Phillips, Katz, Clark & Mortimer

(57) ABSTRACT

The present invention relates to pharmaceutical compositions containing at least one protein active ingredient protected from digestive enzymes. The pharmaceutical compositions contain the at least one protein active ingredient, in free form, as well as, for liquids, a system that buffers them to a pH greater than 4 and less than or equal to 8 or, for solids, a system that exerts, when they are placed in a liquid medium, a buffer effect between a pH greater than 4 and a pH less than or equal to 8.

45 Claims, 1 Drawing Sheet

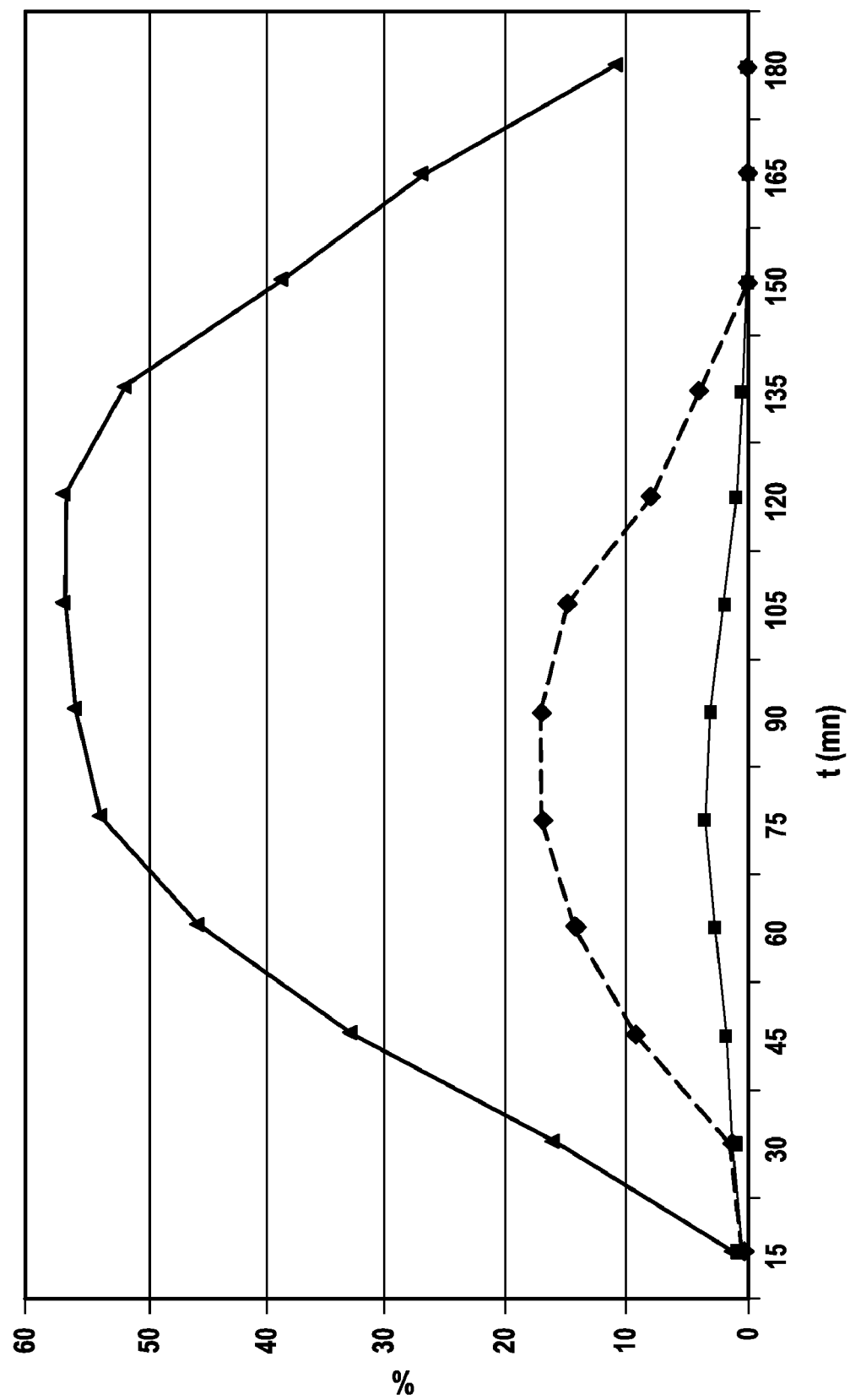

PHARMACEUTICAL COMPOSITIONS AND METHODS FOR THE ORAL DELIVERY OF INSULIN

BACKGROUND OF THE INVENTION

To date, protein active ingredients, thus sensitive to digestive enzymes, in particular insulin and analogues thereof (more precisely sensitive to proteases, such as pepsin in the stomach and principally trypsin in the intestine), remain essentially administered by parenteral route in spite of numerous studies that have been undertaken to investigate alternate routes of delivery (in particular those more comfortable for patients).

The article by Simona Cernea and Itamar Raz, published in Timely Top. Med. Cardiovasc. Dis. 2006 Nov. 1; Vol 10: E29, summed up, in 2006, alternatives to administering insulin by injection. A number of patent documents, for example WO 85/05029, U.S. Pat. No. 5,824,638 and WO 2006/127361, also exist on the subject.

The most advanced work is probably that relating to administration by nasal route. This route of administration would indeed be less technically constraining than the parenteral route. The highly vascular nasal mucosa has the capacity to absorb proteins and to transmit them to the blood system, which makes it a potentially good candidate. However, it suffers from a certain difficulty in controlling the dose delivered by inhalers depending on the patient (notably if the patient has a cold, etc.).

According to the prior art, protein active ingredients that have been chemically modified according to numerous variants and those formulated according to numerous variants have more generally been disclosed. Thus:

U.S. Pat. No. 4,692,433 discloses administration by oral route of polypeptide hormones. Said hormones are administered, advantageously in buffered aqueous solutions, encapsulated in a liposome. They are not administered in free form;

documents WO 97/33531, WO 02/072075 and US 2003/0017203 disclose gastro-resistant forms for the administration of peptides by oral route. These forms combine a gastro-resistant coating and a pH-lowering agent. Said coating protects the active ingredient during its passage in the stomach. Once in the intestine, said coating is dissolved, releasing both the active ingredient and the pH-lowering agent. Due to the action of said pH-lowering agent, the pH of the intestine is lowered locally, in fact reducing the proteolytic activity of the intestinal proteases present. Protection in the stomach and in the entry of the intestine is thus ensured by two different means whose action develops successively. The peptides in question intervene neither in free form nor in the presence of a buffer. Incidentally, it should be noted here that table 1 on page 23 of application WO 97/33531 presents results for the bioavailability of buffered solutions of calcitonin. The tests were conducted to study the influence of the pH of the solution administered locally (directly in the intestine of rats) on the absorption of the active ingredient. These tests were conducted in order to optimize the nature of the pH-lowering agent intervening in the gastro-resistant form proposed. These tests neither describe nor suggest the oral compositions of the invention (pharmaceutical compositions or drugs) disclosed below;

application US 2002/0132757 relates to the administration of calcitonin, in the form of solid particles, through epithelial membranes, through oral or nasal mucosa. For this specific type of administration, which does not involve the gastrointestinal tract, the active ingredient is treated as follows. It is first dissolved in a buffer (mere processing aid). The solution obtained, supplemented with one or more surfactants and one or more absorption enhancers, is lyophilized. The dry particles obtained are finally packaged in a pressurized container with a suitable solvent or vehicle (ethanol, for example). The function of this solvent or vehicle is to disperse under pressure said particles over an area, as large as possible, of the mucosae. Said particles are not administered in the presence of a buffer;

application US 2007/0154559 discloses a complicated method of formulating active ingredients for administration by oral route. Improved gastrointestinal absorption is sought. The absorption in question is that of nanoparticles containing said active ingredients. According to the method disclosed, the active ingredient is first dissolved in a buffer (mere processing aid) and then complexed with a counter ion. The complex obtained is placed in solution, in the presence of a polymer and a lipid, in an organic solvent. An emulsion is then generated with the obtained organic solution and an aqueous solution containing an emulsifier. The nanoparticles are finally formed by the evaporation of said organic solvent. Thus, the active ingredient is administered neither in free form nor in the presence of a buffer;

application WO 2007/032018 discloses a complicated method of formulating active ingredients, for administration by oral route, of the same type as disclosed in the US application above. The active ingredient is also delivered in nanoparticle form. Said nanoparticles (fatty acid and polymer-based) are sensitive to pH. They shrink in acidic pH. The active ingredient is thus better protected during its passage in the stomach. Here again, the active ingredient is administered neither in free form nor in the presence of a buffer;

application FR 2,123,524 (corresponding Irish Patent Application No. IE36225B1) discloses an insulin derivative obtained by acylation. The chemical reaction in question is implemented in a buffered medium. Application WO 01/36656 discloses a complex between a biomolecule and hyaluronic acid. These two documents of the prior art neither disclose nor suggest pharmaceutical compositions combining their active ingredient in free form and a protective buffer system.

The above comments summarize the prior art teaching with respect to the concepts of oral composition, free-form protein active ingredient and buffer. Thus there is a need for a composition for the oral delivery of a protein active ingredient that resists being metabolized in the gastric environment and in the intestinal environment.

BRIEF SUMMARY OF THE INVENTION

In a first aspect, the invention provides a pharmaceutical composition, in liquid or solid form, for administration by oral route of at least one protein active ingredient. In embodiments according to this aspect, the composition comprises at least one protein active ingredient, in free form, and, for a liquid, a buffer system that buffers it to a pH greater than 4 and less than or equal to 8 or, for a solid, a buffer system that exerts, when it is placed in a liquid medium, a buffer effect between a pH greater than 4 and a pH less than or equal to 8. The term "protein active ingredient" means a protein or peptide that substantially retains its biological activity after passage through the stomach and intestine.

In a second aspect, the invention provides a pharmaceutical composition according to the first aspect, obtained by the formulation of at least one protein active ingredient in free form with a system that buffers it, in liquid form, to a pH greater than 4 and less than or equal to 8 or, in solid form, with a system that exerts, when said solid form is placed in a liquid medium, a buffer effect between a pH greater than 4 and a pH less than or equal to 8.

In a third aspect, the invention provides a method for preparing a pharmaceutical composition, in liquid or solid form, for the oral delivery of at least one protein active ingredient. In embodiments according to this aspect of the invention, the method comprises the formulation of at least one protein active ingredient in free form with a buffer system that buffers said composition, in liquid form, to a pH greater than 4 and less than or equal to 8, or in solid form, with a buffer system that exerts, when placed in a liquid medium, a buffer effect between a pH greater than 4 and a pH less than or equal to 8.

In a fourth aspect, the invention provides a method for treating a disease or disorder in a patient. In embodiments according to this aspect, the method comprises orally administering to the patient a pharmaceutical composition, in liquid or solid form, comprising at least one protein active ingredient in free form, and, for a liquid, a buffer system that buffers it to a pH greater than 4 and less than or equal to 8 or, for a solid, a buffer system that exerts, when it is placed in a liquid medium, a buffer effect between a pH greater than 4 and a pH less than or equal to 8.

In a fifth aspect, the invention provides a method for providing at least protein active ingredient, in liquid or solid form, for oral delivery to a patient. In embodiments according to this aspect, the method comprises orally administering to the patient at least one protein active ingredient in free form, and, for a liquid, a buffer system that buffers it to a pH greater than 4 and less than or equal to 8 or, for a solid, a buffer system that exerts, when it is placed in a liquid medium, a buffer effect between a pH greater than 4 and a pH less than or equal to 8.

BRIEF DESCRIPTION OF THE DRAWINGS

FIG. 1 depicts the percentage of decrease in glycemia as a function of time (expressed in minutes) for the in vivo test as described below.

DETAILED DESCRIPTION OF THE PREFERRED EMBODIMENTS

The principal object of the present invention is compositions—compositions for use as a drug or pharmaceutical compositions—containing at least one protein active ingredient protected from digestive enzymes. Within said compositions, said at least one active ingredient is formulated in such a way as to resist being metabolized in the gastric environment and in the intestinal environment. Said compositions are compositions for administration by oral route (via the gastrointestinal tract) of said at least one protein active ingredient (sensitive to digestive enzymes).

The technical problem of administering by oral route a protein active ingredient (thus sensitive to digestive enzymes) is dual insofar as the system of protection provided must a priori be effective in both the stomach and in the entry of the intestine. It must a priori first resist the gastric juice and then the pancreatic juice. Indeed, at the exit of the stomach, in the pylorus, when acid chyme flows in the duodenum, secretin is released from the intestine and stimulates the pancreas to secrete both bicarbonate (in order to decrease the acidity of said chyme) and cholecystokinin (pancreozymin), which stimulates the secretion of pancreatic juice rich in enzymes (trypsinogen and chymotrypsinogen, transformed into trypsin and chymotrypsin activated by an enterokinase). Once acidity is neutralized in the duodenum by the hydrocarbonated secretin, feedback and inhibition of pancreatic secretions then occur. This normal digestive mechanism is familiar to those skilled in the art.

Confronted with said technical problem of administering by oral route a protein active ingredient, the inventors propose a completely novel solution, not based on a dual system of protection but on a system of protection in the stomach that also inhibits pancreatic secretion (which eliminates the problem of degradation of the active ingredient in the entry of the intestine). The inventors propose a posteriori this explanation on the good results obtained with the compositions of the invention. The novel system of protection proposed is a buffer system. In a completely surprising manner, said novel system of protection, a buffer system, enables the administration, by oral route (via the gastrointestinal tract), of the protein active ingredient, in free form.

According to its first object, the present invention thus relates to novel compositions for use as a drug or pharmaceutical compositions, intended for (suitable for) the administration by oral route of at least one protein active ingredient; said compositions being buffered.

More precisely, the compositions of the invention are provided in liquid or solid form. Said compositions are oral compositions containing at least one protein active ingredient. They are suitable for administration by oral route of said active ingredient.

Characteristically, said compositions are:
liquids, containing a system (a buffer system) that buffers them at a pH greater than 4 and less than or equal to 8;
solids, containing a system (a buffer system) that exerts, when they are placed in a liquid medium, generally aqueous, a buffer effect between a pH greater than 4 and a pH less than or equal to 8.

According to its first object, the present invention thus relates to:
pharmaceutical compositions, in liquid or solid form, for administration by oral route (via the gastrointestinal tract), containing at least one protein active ingredient, which contains said protein active ingredient, in free form, as well as, for liquids, a system (a buffer system) that buffers them to a pH greater than 4 and less than or equal to 8 or, for solids, a system (a buffer system) that exerts, when they are placed in a liquid medium, a buffer effect between a pH greater than 4 and a pH less than or equal to 8.

Said compositions of the invention are obtained by formulation of said at least one protein active ingredient in free form with a system (a buffer system) capable of buffering them, in liquid form, at a pH greater than 4 and less than or equal to 8 or, in solid form, with a system (a buffer system) that exerts, when said solid form is placed in a liquid medium, a buffer effect between a pH greater than 4 and a pH less than or equal to 8.

Characteristically, the liquid or solid (monophasic (single phase), in any event) compositions of the invention are oral compositions that combine within them at least one protein active ingredient in free form and a buffer system. Said buffer system enables, as indicated above, administration by oral route of the protein active ingredient, in free form. It is effective in protecting said free form in the gastrointestinal tract.

Within the compositions of the invention, the protein active ingredient is thus present "as is", not per se protected, notably not protected by a physical barrier. It is present as is or in a simple mixture with the excipients required for its formulation. "Free form of said active ingredient" means most notably said active ingredient without a physical system of protection, more or less complex, such as a coating, matrix or capsule wall (said active ingredient is not coated, matrixed or encapsulated (notably in liposomes), etc.).

The buffer system, given the pH values set forth, is capable of buffering the compositions of the invention in gastric environment and in intestinal environment. It is of course capable of exerting its buffer effect for the duration of digestion: for at least 2 hours, advantageously up to 3 hours (in the acidic conditions of the stomach and the basic conditions of the intestine). Those skilled in the art are familiar with such buffer systems. As a nonrestrictive example, the nature of such systems is specified below.

The compositions of the invention combine:
at least one protein active ingredient in free form (see above), generally one such active ingredient (but the combined intervention of several active ingredients of this type (or of at least one active ingredient of this type and at least one other active ingredient), in mixture or separately, is not excluded from the scope of the invention); and
a system (a buffer system) that exerts a buffer effect in the pH range stated above.

The exertion of said buffer effect in said pH range ($4<pH \leq 8$) is of course compatible with the stability of said at least one protein active ingredient (in any event with the stability of the active ingredient(s) present).

The compositions of the invention are buffered to a pH: $4<pH \leq 8$. They are advantageously buffered to a pH between 4.5 and 7.5 ($4.5 \leq pH \leq 7.5$), highly advantageously buffered to a pH between 5 and 7 ($5 \leq pH \leq 7$), indeed to a pH greater than 5 and less than or equal to 7 ($5<pH \leq 7$). In a particularly preferred variant, they are buffered to a pH of 6.5 or close to 6.5 (6.5±0.2). This value is quite particularly preferred in the context of a composition of the invention containing insulin.

The compositions of the invention contain at least one protein active ingredient, which they protect from digestive enzymes. Insulin has already been mentioned as one such active ingredient sensitive to digestive enzymes. The invention was developed specifically in reference to this active ingredient (see the examples and tests presented below). Those skilled in the art clearly understand, however, that its field of application is undoubtedly broader. The mechanism a priori concerned (that the inventors propose a posteriori)—protection during passage in the stomach (at pH>4 pepsin is no longer (or practically no longer) active) and inhibition (more or less consequent) of pancreatic secretions insofar as acid chyme no longer flows in the duodenum—is suitable to protect all protein active ingredients from digestive enzymes.

Thus, the compositions of the invention contain, advantageously, at least one protein active ingredient (in free form) selected among insulin, its analogues and derivatives thereof (generally and advantageously contain insulin or an analogue or derivative thereof as a single active ingredient of this type, or as a single active ingredient). Those skilled in the art are familiar with insulin analogues such as, for example, Lispro insulin, Aspart insulin, Glargine insulin and Detemir insulin. Those skilled in the art are also familiar with insulin derivatives such those described in application FR 2,123,524.

Thus, the compositions of the invention contain, advantageously, as active ingredient (in free form):
insulin or an analogue or derivative thereof,
somatotropin (human growth hormone) or a derivative thereof,
calcitonin, or
an LHRH (Luteinizing Hormone Releasing Hormone) analogue such as tryptoreline.

Recall that the compositions of the invention may contain several of these active ingredients and that the list above, far from being exhaustive, is in no way restrictive.

The buffer systems suitable for purposes of the invention are classical buffer systems, advantageously of high capacity. Those skilled in the art are familiar with such systems and are capable of optimizing a combination in the context of the invention: at least one protein active ingredient (in free form)/buffer system (for example: insulin/buffer system).

In a completely nonrestrictive way, it can be stated that the system responsible for the buffer effect within the compositions of the invention is advantageously a buffer chosen among phosphate, acetate, maleate, phthalate, succinate, citrate, imidazole, tetrabutylammonium, 2-amino-2-hydroxymethyl-1,3-propanediol (or trihydroxymethylaminomethane or Trometamol or Tham or Tris), tris-glycine, barbitol, tris-EDTA BSA, copper sulfate and zwitterionic buffers.

More generally, the buffer system of the compositions of the invention can be selected among the list of buffer systems given in the European Pharmacopeia, current edition (monograph 4.1.3).

Said buffer system is advantageously a phosphate or Tris buffer.

A suggested phosphate buffer contains:
from 2 to 3% by weight sodium dihydrogen phosphate, and
from 97 to 98% by weight disodium hydrogen phosphate, and advantageously contains:
about 2.8% by weight sodium dihydrogen phosphate, and
about 97.2% by weight disodium hydrogen phosphate.

The oral compositions of the invention (combining in a novel way at least one protein active ingredient, in free form, and the selected system buffer: $4<pH \leq 8$) can exist according to two variants.

According to a first, more classical variant, said compositions are formulated in unit form. All of the constitutive ingredients, including the buffer system, are formulated together. Within the scope of this first variant, many possibilities exist. The compositions of the invention can notably be provided in liquid forms (directly buffered to a suitable pH) such as solutions, suspensions and syrups, or in solid forms (which develop the buffer effect, when consumed, in a liquid, generally water, or following their consumption, in the stomach) such as tablets (classical (to be swallowed), to be sucked, sublingual, dispersible, orodispersible, effervescent), capsules, powders, effervescent powders, granules, effervescent granules and lyophilisates. These lists are not exhaustive. Those skilled in the art know how to formulate, in one or the other of the unit forms listed above, the active ingredient in question with a suitable system responsible for the buffer effect sought.

In the preparation of effervescent pharmaceutical forms, it is advisable to add ingredients that provide the effervescent character expected. These types of ingredients (reagents (generally two reagents) that react by releasing gas) are familiar to those skilled in the art.

Within the scope of this first variant, the compositions of the invention are advantageously provided as solid pharmaceutical preparations, in particular dispersible tablets or effervescent tablets.

According to a second variant, the compositions of the invention are compositions with at least two separate components, notably compositions that comprise separately:
one component containing at least one protein active ingredient in free form; and another component containing at least one system that generates the buffer effect desired.

These two, separate, components are to be administered jointly or quasi jointly, in such a way, of course, that the buffer effect develops during the passage of the active ingredient in the digestive tract (first of all in the stomach).

The compositions of the invention (according to the first or second variant above) containing said at least one protein active ingredient in free form (or said at least one protein active ingredient in free form and at least one other active ingredient) and the joined system buffer, generally in a pharmaceutically acceptable excipient (with, if necessary, ingredients that make them effervescent), may of course contain other ingredients that are present in classical pharmaceutical compositions, such as sweeteners, flavors and/or processing aids (lubricants, etc.). Liquid compositions may contain only said at least one protein active ingredient (or said at least one protein active ingredient in free form and at least one other active ingredient) and the suitable system buffer. They generally contain, in addition to these two components, formulation ingredients classically used in pharmaceutical formulations (such as the ingredients listed above). Solid compositions generally contain, in addition to said at least one protein active ingredient (or in addition to said at least one protein active ingredient in free form and at least one other active ingredient) and the buffer system, a solid excipient (base, optionally with ingredients responsible for effervescence) with various additives (such as the ingredients listed above).

Preparation of the Compositions of the Invention, in Unit Forms or not, as described above, constitutes the second object of the present invention. Said preparation is a preparation of a pharmaceutical composition that is buffered or that is combined with a buffer. Characteristically, it comprises the (simple) formulation of at least one protein active ingredient in free form with a system (a buffer system) that buffers said composition in liquid form (notably in the gastric environment and in the intestinal environment) at a pH greater than 4 and less than or equal to 8 or, in solid form, with a system (a buffer system) that exerts, when placing said solid form in a liquid medium, notably an aqueous medium (notably in the gastric environment and in the intestinal environment), a buffer effect between a pH greater than 4 and a pH less than or equal to 8. The term "formulation" should be taken in the classical sense of the term (galenic) for the preparation of unit compositions, and in the broader sense (formulation=packaging) for the preparation of compositions with separate components.

Conventionally, other ingredients may be included in the preparation of the compositions of the invention.

Those skilled in the art understand the importance of the present invention, which is confirmed by the examples and test results presented below. The "dual positive effect" of the buffer—gastroprotection and inhibition of pancreatic secretions—is particularly effective. This dual effect and its effectiveness are genuinely surprising.

According to another of its aspects, the invention provides a new application for buffer systems and thus also relates to the use of a buffer system as specified above, notably selected among those identified above, to protect at least one protein active ingredient in free form during its passage via the gastrointestinal tract. In other words, the invention provides a novel method for protecting, with respect to digestive enzymes (during gastrointestinal passage), protein active ingredients. Said method essentially comprises the formulation, in unit form or not, of said active ingredients in free form, with a buffer system such as specified above, notably selected among those identified above.

Finally, the invention can be seen as a method of therapeutic treatment comprising the administration by oral route of at least one protein active ingredient and/or a method of oral administration of at least one protein active ingredient. Characteristically, in the context of said method, said at least one active ingredient is administered (formulated in a solid or liquid composition, unit form or not), in free form, with a buffer system as specified above, i.e., buffered to a pH as specified above, $4<pH\leq8$ (in the case of a liquid form), or able to be buffered to such a pH when it is placed in a liquid medium (in the case of a solid form). The concerned today known treatments are those of the diseases or disorders hereafter precised: diabetes (in reference to the administration if insulin), growth inhibition (in reference to the administration of somatropin), osteoporosis (in reference to the administration of calcitonin), prostate cancer (in reference to the administration of LHRH) . . . .

The invention will now be illustrated by specifying, on a purely illustrative basis, the formula for two buffered insulin tablets of the invention, and the great interest of said invention will be shown by presenting below the comparative results of physicochemical tests conducted in vitro and pharmacological tests conducted in vivo with insulin.

I Formulas

Two types of tablets of the invention were prepared, according to a method known per se (classical formulation method), from the ingredients indicated, used in the quantities indicated:

dispersible tablets A; and effervescent tablets B.

| Tablets A: | |
|---|---|
| human insulin | 3.5 mg (100 U) |
| trometamol (TRIS) | 100 mg |
| calcium phosphate (dicalcic) | 250 mg |
| microcrystalline cellulose | 250 mg |
| mannitol | 250 mg |
| magnesium stearate | 10 mg |
| colloidal silica | 1 mg |
| crospovidon | 50 mg |
| sodium benzoate | 30 mg |
| Talc | 10 mg |
| citric acid | q.s. pH 6.5 |
| monosodium citrate | |
| tablet weight: 1 gram | |

| Tablets B: | |
|---|---|
| human insulin | 3.5 mg (100 U) |
| anhydrous monosodium citrate | 1142.7 mg |
| anhydrous sodium bicarbonate | 2076 mg |
| sodium benzoate | 152.60 mg |
| monosodium phosphate and disodium phosphate | 120 mg |
| ethanol 96% | q.s. for granulation |
| demineralized water | |
| for a tablet of theoretical weight: | 3.5 g |
| in solution pH 6.8. | |

II In Vitro Tests

Tests were conducted in vitro to confirm the metabolic role of pepsin in an acid medium, the metabolic role of trypsin in a basic medium and the inactivation of one and the other of these digestive enzymes in a buffered medium according to the invention.

During these various tests, the insulin was assayed by liquid chromatography.

Test 1'
Human insulin solution (100 U) + 0.1 N HCl (50 ml) pH 1 + stirring at 37° C. for 1 h, 2 h, 3 h

| Time | Insulin content |
|---|---|
| Time 0 | 99.00 U |
| 1 h | 99.87 U |
| 2 h | 100.13 U |
| 3 h | 100.30 U |

In an acid medium, at pH 1, without pepsin, the insulin is stable for more than 3 hours at 37° C.

Test 2'
Human insulin solution (100 U) + 0.1 N HCl (50 ml) pH 1 + pepsin (160 mg) + stirring at 37° C. for 1 h

| Time | Insulin content |
|---|---|
| Time 0 | 0 U |
| 1 h | 0 U |

In the presence of the gastric enzyme (pepsin), at pH 1, the insulin is immediately degraded.

Test 1 (invention)
Human insulin solution (100 U) + 0.1 N HCl (50 ml) pH 1 + pepsin (160 mg) + phosphate buffer pH 6.8 (50 ml) + stirring at 37° C. for 1 h, 2 h, 3 h

| Time | Insulin content |
|---|---|
| Time 0 | 101.32 U |
| 1 h | 101.73 U |
| 2 h | 99.72 U |
| 3 h | 101.60 U |

In a medium buffered to pH 6.8, the pepsin is no longer activated and the insulin is stable for more than 3 hours at 37° C.

Test 3'
Human insulin solution (100 U) + 0.1 N HCl + phosphate buffer pH 8.5 + stirring at 37° C. for 1 h, 2 h, 3 h

| Time | Insulin content |
|---|---|
| Time 0 | 100 U |
| 1 h | 99.59 U |
| 2 h | 100.24 U |
| 3 h | 100.48 U |

This test verified the effectiveness of the buffer and the fact that in the absence of enzyme, the insulin is stable in a basic medium.

Tests 2a, 2b, 2c (invention)
Human insulin solution (100 U) + phosphate buffer
pH 6 (test 2a), pH 6.5 (test 2b), pH 6.8 (test 2c) + trypsin
750 U + stirring at 37° C. for 1 h, 2 h

| | Insulin content | | |
|---|---|---|---|
| Time | pH 6 | pH 6.5 | pH 6.8 |
| Time 0 | 100 U | 100 U | 98 U |
| 1 h | 92 U | 83 U | 56 U |
| 2 h | 86 U | 72 U | 48 U |

In a medium buffered to the indicated pH, the metabolic effect of the trypsin is mostly attenuated.

Test 4'
Human insulin solution (100 U) + phosphate buffer pH 8.5 + trypsin 750 U + stirring at 37° C. for 1 h, 2 h

| Time | Insulin content |
|---|---|
| Time 0 | 89 U |
| 1 h | 14.5 U |
| 2 h | 1.5 U |

In the presence of the intestinal enzyme (trypsin), at pH 8.5, the insulin is strongly degraded.

Examination of these results (at basic pH) shows that the more the pH increases toward alkalinity, the more the trypsin exerts its metabolic effect.

The optimum point seems to be pH 6.5 (near neutral pH) where after 2 hours, in spite of the presence of trypsin, a high percentage of insulin is found: 72%.

III In Vivo Tests

The hypoglycemic activity of two types of effervescent tablets (with a buffer system of the invention: tablets B (see above) and without a buffer system of the invention: control effervescent tablets (tablets B but without a buffer)) was studied in rats rendered diabetic (hyperglycemic) by administration of streptozotocin.

Streptozotocin, an antibiotic chemically related to the nitrosoureas, has diabetogenic properties by the destruction of the islets of Langerhans of the pancreas.

The test is quite familiar to those skilled in the art. Its principle is summarized below.

Administration in male Wistar rats (mean weight 200 g) by intraperitoneal route of 70 mg/kg of streptozotocin causes in the animal after 72 h severe hyperglycemia combined with polyphagia, polydipsia and polyuria.

The animals are divided into three batches of eight.

Batch 1: normal animals, non-hyperglycemic, receiving by oral route using an esophageal probe 30 units of insulin contained in a tablet buffered to pH 6.8 (effervescent tablet B (see above)), in a volume of 10 ml/kg.

Batch 2: diabetic animals, receiving by oral route using an esophageal probe 30 units of insulin contained in a non-buffered tablet (effervescent tablet B but without buffer), in a volume of 10 ml/kg.

Batch 3: diabetic animals, receiving by oral route using an esophageal probe 30 units of insulin contained in a tablet buffered to pH 6.8 (effervescent tablet B (see above)), in a volume of 10 ml/kg.

Blood samples are drawn every 15 minutes for 3 hours from the tail of the animal and glycemia is evaluated using an Abbott glucose meter.

The results are presented in the tables below. They are expressed in grams of glucose per liter and also in milliequivalents (table 1), and as a percentage decrease in glycemia (table 2).

TABLE 1

| | | Glycemia (g/l and meq/l) | | | | | | |
|---|---|---|---|---|---|---|---|---|
| | | Time in min | | | | | | |
| | | 0 | 15 | 30 | 45 | 60 | 75 | 90 |
| Batch 1 | g/l | 0.99 ± 0.04 | 0.99 ± 0.03 | 0.98 ± 0.05 | 0.90 ± 0.03 | 0.85 ± 0.04 | 0.82 ± 0.05 | 0.82 ± 0.06 |
| | meq/l | 5.50 ± 0.2 | 5.50 ± 0.16 | 5.45 ± 0.3 | 5 ± 0.16 | 4.72 ± 0.2 | 4.56 ± 0.3 | 4.56 0.33 |
| Batch 2 | g/l | 3.94 ± 0.18 | 3.92 ± 0.16 | 3.91 ± 0.16 | 3.88 ± 0.15 | 3.84 ± 0.16 | 3.81 ± 0.14 | 3.82 ± 0.15 |
| | meq/l | 22 ± 1 | 21.7 ± 0.9 | 21.7 ± 0.9 | 21.6 ± 0.8 | 21.3 ± 0.9 | 21.2 ± 0.8 | 21.2 ± 0.8 |
| Batch 3 | g/l | 3.8 ± 0.5 | 3.7 ± 0.5 | 3.2 ± 0.4 | 2.5 ± 0.3 | 2.5 ± 0.4 | 1.76 ± 0.3 | 1.64 ± 0.4 |
| | meq/l | 21.1 ± 2.8 | 20.6 ± 2.8 | 17.8 ± 2.2 | 14 ± 1.7 | 11.4 ± 2.2 | 9.8 ± 1.7 | 9.1 ± 2.2 |
| | | Time in min | | | | | | |
| | | 105 | 120 | 135 | 150 | 165 | 180 | |
| Batch 1 | g/l | 0.84 ± 0.06 | 0.91 ± 0.05 | 0.95 ± 0.04 | 0.99 ± 0.03 | 1.01 ± 0.02 | 0.99 ± 0.03 | |
| | meq/l | 4.7 ± 0.33 | 5 ± 0.16 | 5.3 ± 0.2 | 5.50 ± 0.16 | 5.6 ± 0.1 | 5.5 ± 0.16 | |
| Batch 2 | g/l | 3.87 ± 0.13 | 3.91 ± 0.14 | 3.94 ± 0.15 | 3.95 ± 0.15 | 3.95 ± 0.16 | 3.92 ± 0.17 | |
| | meq/l | 21.5 ± 0.7 | 21.7 ± 0.8 | 21.9 ± 0.8 | 21.9 ± 0.8 | 21.9 ± 0.9 | 21.8 ± 0.9 | |
| Batch 3 | g/l | 1.6 ± 0.4 | 1.65 ± 0.5 | 1.8 ± 0.5 | 2.3 ± 0.6 | 2.78 ± 0.8 | 3.4 ± 0.8 | |
| | meq/l | 8.9 ± 2.2 | 9.2 ± 2.8 | 10 ± 2.8 | 12.8 ± 3.3 | 15.4 ± 4.5 | 19 ± 4.5 | |

TABLE 2

| | % decrease in glycemia | | | | | | | | | | | |
|---|---|---|---|---|---|---|---|---|---|---|---|---|
| | Time in min | | | | | | | | | | | |
| | 15 | 30 | 45 | 60 | 75 | 90 | 105 | 120 | 135 | 150 | 165 | 180 |
| Batch 1 | 0 | 1 | 9 | 14 | 17 | 17 | 15 | 8 | 4 | 0 | 0 | 0 |
| Batch 2 | 0.50 | 0.75 | 1.5 | 2.5 | 3.3 | 3 | 1.8 | 0.75 | 0.50 | 0 | 0 | 0 |
| Batch 3 | 1 | 16 | 33 | 46 | 54 | 56 | 57 | 57 | 52 | 39 | 27 | 11 |

The results from table 2 were plotted on the single FIGURE in the appendix (percentage of decrease in glycemia as a function of time (expressed in minutes)):
the -■- curve shows the results of batch 1,
the --♦-- curve shows the results of batch 2,
the -▲- curve shows the results of batch 3.
Examination of the results shows:
in the normal (non-hyperglycemic) animals (batch 1), administration of buffered insulin leads after 45 minutes to a slight decrease in glycemia with a maximum at the $75^{th}$ minute, and then glycemia returns to normal values after the $150^{th}$ minute. These animals, with the pancreas intact, compensate by secreting glucagon, which is a hyperglycemic;
in the diabetic animals (batch 2), administration of non-buffered insulin leads to a very slight, insignificant decrease in glycemia. Throughout the experiment, the animals maintain very high glycemia;
in the diabetic animals (batch 3), administration of buffered insulin leads after 45 minutes to a highly significant decrease in glycemia with a maximum at the $105^{th}$ minute, and then a progressive increase in glycemia is observed. All the animals are highly improved, although they do not return to normal glycemia due to the severity of the diabetes.
These results show that the buffer system used made it possible to preserve the hypoglycemic activity of the insulin administered by oral route (which is completely consistent with the results obtained in vitro) and confirm the good bioavailability of said insulin.

The results, both in vitro and in vivo, demonstrate the effectiveness of the buffer system in preserving the activity of insulin:
in vitro
in an acid medium, non-buffered, the insulin is metabolized by the pepsin (test 2'). In a medium buffered to pH 6.8, the pepsin is no longer active and as a result 100% of the insulin is found after 3 hours (test 1),
in a basic medium, the insulin is metabolized by the trypsin (test 4'). In media buffered to pH 6, 6.5 and 6.8, the activity of said trypsin is inhibited, more or less decreased;
in vivo
the non-buffered preparation exhibits practically no activity. In contrast, the buffered preparation exhibits strong hypoglycemic activity.
In all the tests, both in vitro and in vivo, human insulin was used. It is evident that the results obtained are applicable to all insulin analogues.
Considering these results, the importance of the present invention is quite obvious. This importance has been confirmed by preliminary tests in man.

The invention claimed is:
1. A pharmaceutical composition, in tablet form, for administration of at least one protein active ingredient sensitive to digestive enzymes, comprising at least one protein active ingredient selected from insulin, Lispro insulin, Aspart insulin, Glargine insulin or Detemir insulin, and a buffer system capable of protecting the protein active ingredient from digestive enzymes and buffering the composition to a pH greater than, or equal to, 5 and less than, or equal to, 7, wherein the composition is free of any component; other than the buffer system, that acts to protect the active ingredient from the digestive enzymes.

2. The pharmaceutical composition according to claim 1, wherein the buffer system is selected from phosphate, acetate, maleate, phthalate, succinate, citrate, imidazole, tetrabutylammonium, trihydroxymethylaminomethane, tris-glycine, barbitol, tris-EDTA, BSA, copper sulfate or zwitterionic buffers.

3. The pharmaceutical composition according to claim 1, wherein the composition is formulated in unit form.

4. The pharmaceutical composition according to claim 1, wherein the buffer system is formulated separately from the at least one protein active ingredient.

5. The pharmaceutical composition according to claim 1, wherein the buffer pH is 6.5+/−0.2.

6. The pharmaceutical composition according to claim 1, wherein the buffer system is a phosphate buffer.

7. The pharmaceutical composition according to claim 1, wherein the at least one protein active ingredient is insulin.

8. The pharmaceutical composition according to claim 1, wherein the at least one protein active ingredient is insulin, the buffer system is a phosphate buffer and the buffer pH is 6.5+/−0.2.

9. The pharmaceutical composition according to claim 1, wherein the at least one protein active ingredient is insulin, the buffer system is a phosphate buffer and the buffer pH is 6.8.

10. The pharmaceutical composition according to claim 1, wherein the at least one protein active ingredient is Lispro insulin, Aspart insulin, Glargine insulin or Detemir insulin.

11. The pharmaceutical composition according to claim 1, wherein the tablet form is in a dispersible tablets form.

12. The pharmaceutical composition according to claim 1, wherein the tablet form is in an effervescent tablets form.

13. The pharmaceutical composition according to claim 1, wherein the at least one protein active ingredient is Lispro insulin, Aspart insulin, Glargine insulin or Detemir insulin, the buffer system is a phosphate buffer and the buffer pH is 6.5+/−0.2.

14. A method for administering at least one protein active ingredient, which is sensitive to digestive enzymes, to a patient suffering from diabetes, wherein the at least one protein active ingredient is selected from insulin, Lispro insulin, Aspart insulin, Glargine insulin or Detemir insulin, the method comprising administering a pharmaceutical composition in tablet form comprising at least one protein active ingredient and a buffer system capable of buffering the composition to a pH greater than, or equal to, 5 and less than, or equal to, 7; wherein the composition is free of any component, other than the buffer system, that acts to protect the active ingredient from the digestive enzymes.

15. The method according to claim 14, wherein the at least one protein active ingredient is insulin.

16. The method according to claim 14, wherein the at least one protein active ingredient is Lispro insulin, Aspart insulin, Glargine insulin or Detemir insulin.

17. The method according to claim 14, wherein the buffer system is selected from phosphate, acetate, maleate, phthalate, succinate, citrate, imidazole, tetrabutylammonium, trihydroxymethylaminomethane, tris-glycine, barbitol, tris-EDTA, BSA, copper sulfate or zwitterionic buffers.

18. The method according to claim 14, wherein the buffer system is a phosphate buffer.

19. The method according to claim 14, wherein the buffer pH is 6.5+/−0.2.

20. The method according to claim 14, wherein the at least one protein active ingredient is insulin, the buffer system is a phosphate buffer and the buffer pH is 6.5+/−0.2.

21. The method according to claim 14, wherein the at least one protein active ingredient is Lispro insulin, Aspart insulin, Glargine insulin or Detemir insulin, the buffer system is a phosphate buffer and the buffer pH is 6.5+/−0.2.

22. The method according to claim 14, wherein the composition is formulated in unit form.

23. The method according to claim 14, wherein the tablet form is in a dispersible tablets form.

24. The method according to claim 14, wherein the tablet form is in an effervescent tablets form.

25. The method according to claim 14, wherein the buffer system is formulated separately from the at least one protein active ingredient.

26. A method for reducing glycemia in a patient suffering from diabetes, the method comprising administering a pharmaceutical composition in tablet form comprising at least one protein active ingredient which is sensitive to digestive enzymes and is selected from insulin, Lispro insulin, Aspart insulin, Glargine insulin or Detemir insulin and a buffer system capable of buffering the composition to a pH greater than, or equal to, 5 and less than, or equal to, 7, wherein the composition is free of any component, other than the buffer system, that acts to protect the active ingredient from the digestive enzymes.

27. The method according to claim 26, wherein the at least one protein active ingredient is insulin.

28. The method according to claim 26, wherein the at least one protein active ingredient is Lispro insulin, Aspart insulin, Glargine insulin or Detemir insulin.

29. The method according to claim 26, wherein the buffer system is selected from phosphate, acetate, maleate, phthalate, succinate, citrate, imidazole, tetrabutylammonium, trihydroxymethylaminomethane, tris-glycine, barbitol, tris-EDTA, BSA, copper sulfate or zwitterionic buffers.

30. The method according to claim 26, wherein the buffer system is a phosphate buffer.

31. The method according to claim 26, wherein the buffer pH is 6.5+/−0.2.

32. The method according to claim 26, wherein the at least one protein active ingredient is insulin, the buffer system is a phosphate buffer and the buffer pH is 6.5+/−0.2.

33. The method according to claim 26, wherein the at least one protein active ingredient is Lispro insulin, Aspart insulin, Glargine insulin or Detemir insulin, the buffer system is a phosphate buffer and the buffer pH is 6.5+/−0.2.

34. The method according to claim 26, wherein the composition is formulated in unit form.

35. The method according to claim 26, wherein the tablet form is in a dispersible tablet form.

36. The method according to claim 35, wherein the tablet form is in an effervescent tablets form.

37. The method of claim 26, wherein the buffer system is formulated separately from the at least one protein active ingredient.

38. A method for treating diabetes comprising administering to a patient a pharmaceutical composition in tablet form comprising at least one protein active ingredient which is sensitive to digestive enzymes and is selected from insulin, Lispro insulin, Aspart insulin, Glargine insulin or Detemir insulin, and at least one buffer system capable of buffering the composition to a pH greater than, or equal to, 5 and less than, or equal to, 7, wherein the composition is free of any component, other than the buffer system, that acts to protect the active ingredient from the digestive enzymes.

39. A method for orally administering to a patient suffering from diabetes at least one protein active ingredient, the method comprising administering a pharmaceutical composition comprising at least one protein active ingredient, wherein the at least one protein active ingredient is selected from insulin, Lispro insulin, Aspart insulin, Glargine insulin or Detemir insulin, and a buffer system capable of buffering the composition to a pH greater than, or equal to, 5 and less than, or equal to, 7; wherein the composition is free of any component, other than the buffer system, that acts to protect the active ingredient from the digestive enzymes.

40. A method for reducing glycemia in a patient suffering from diabetes comprising orally administering a pharmaceutical composition comprising at least one protein active ingredient which is sensitive to digestive enzymes and is selected from insulin, Lispro insulin, Aspart insulin, Glargine insulin or Detemir insulin, and a buffer system capable of buffering the composition to a pH greater than, or equal to, 5 and less than, or equal to, 7; wherein the composition is free of any component, other than the buffer system, that acts to protect the active ingredient from the digestive enzymes.

41. A solid pharmaceutical composition for oral administration of at least one protein active ingredient sensitive to digestive enzymes, comprising at least one protein active ingredient selected from insulin, Lispro insulin, Aspart insulin, Glargine insulin or Detemir insulin, and a buffer system capable of protecting the protein active ingredient from digestive enzymes and buffering the composition to a pH greater than, or equal to, 5 and less than, or equal to, 7, wherein the composition is free of any component, other than the buffer system, that acts to protect the active ingredient from the digestive enzymes.

42. The method according to claim 39, wherein the buffer pH is about 6.5.

43. The method according to claim 39, wherein the buffer pH is about 6.8.

44. The method according to claim 40, wherein the buffer pH is about 6.5.

45. The method according to claim 40, wherein the buffer pH is about 6.8.

* * * * *